(12) United States Patent
Džakula

(10) Patent No.: US 6,438,204 B1
(45) Date of Patent: Aug. 20, 2002

(54) LINEAR PREDICTION OF STRUCTURE FACTORS IN X-RAY CRYSTALLOGRAPHY

(75) Inventor: Željko Džakula, Rancho Penasquitos, CA (US)

(73) Assignee: Accelrys Inc., San Diego, CA (US)

( * ) Notice: Subject to any disclaimer, the term of this patent is extended or adjusted under 35 U.S.C. 154(b) by 0 days.

(21) Appl. No.: 09/851,358

(22) Filed: May 8, 2001

Related U.S. Application Data

(60) Provisional application No. 60/203,123, filed on May 8, 2000.

(51) Int. Cl.[7] .............................................. G01N 23/207
(52) U.S. Cl. ............................................ 378/73; 378/71
(58) Field of Search ...................................... 378/73, 71

(56) References Cited

U.S. PATENT DOCUMENTS 5,353,236 A * 10/1994 Subbiah ...................... 700/266
6,345,235 B1 * 2/2002 Edgecombe et al. ......... 702/179
6,356,845 B1 * 3/2002 Benson et al. ............... 435/183

OTHER PUBLICATIONS

*An Introduction to X–Ray Crystallography*, Michael M. Woolfson, Cambridge University Press (1970, 1997), Section 8–4, pp. 255–267.

*Numerical Recipes in C, The Art of Scientific Programming*, by W.H. Press, B.P. Flannery, S.A. Teukolsky, and W.T. Vetterling, Cambridge University Press, Cambridge, 1989, pp. 452–464.

"The Use of Wavelet Transforms in Low–Resolution Phase Extension," by J. Wilson and P. Main, Acta. Cryst. vol. D56, pp. 625–633, 2000.

* cited by examiner

*Primary Examiner*—David V. Bruce
*Assistant Examiner*—Pamela R. Hobden
(74) *Attorney, Agent, or Firm*—Knobbe, Martens, Olson & Bear, LLP

(57) ABSTRACT

A method uses linear prediction analysis to define a first structure factor component for a first reflection from x-ray crystallography data. The x-ray crystallography data includes a set of cognizable reflections. The method includes expressing the first structure factor component as a first linear equation in which the first structure factor component is equal to a sum of a first plurality of terms. Each term includes a product of (1) a structure factor component for a cognizable reflection from the x-ray crystallography data, wherein the cognizable reflection has a separation in reciprocal space from the first reflection, and (2) a linear prediction coefficient corresponding to the separation between the cognizable reflection and the first reflection. The method further includes calculating values for the linear prediction coefficients. The method further includes substituting the values for the linear prediction coefficients into the first linear equation, thereby defining the first structure factor component for the first reflection.

16 Claims, 12 Drawing Sheets

LINEAR PREDICTION OF STRUCTURE FACTORS IN X-RAY CRYSTALLOGRAPHY

CROSS REFERENCE TO RELATED APPLICATIONS

This application claims priority under 35 U.S.C. §119(e) to U.S. Provisional Patent Application No. 60/203,123, entitled "Linear Prediction of Structure Factors in X-Ray Crystallography" and filed May 8, 2000.

BACKGROUND OF THE INVENTION

1. Field of the Invention

This invention relates to methods and systems for determining molecular structures using x-ray crystallography.

2. Description of the Related Art

In x-ray diffraction crystallography, a crystalline form of the molecule under study is exposed to a beam of x-rays, and the intensity of diffracted radiation at a variety of angles from the angle of incidence is measured. The beam of x-rays is diffracted into a plurality of diffraction "reflections," each reflection corresponding to a reciprocal lattice vector. From the diffraction intensities of the reflections, the magnitudes of a series of numbers, known as "structure factors," are determined. The structure factors in general are complex numbers, having two components in the complex plane, a magnitude and a phase, and are defined by the electron distribution within the unit cell of the crystal.

The structure factors used to calculate atomic coordinates from measured x-ray diffraction intensities are oscillatory functions of the indices of the reciprocal lattice vectors with an overall decaying envelope. One expression for these structure factors has the following form:

Equation 1:

$$F_{hkl} = \frac{1}{V} \sum_j q_j T_j f_j \{\cos[2\pi(hx_j + ky_j + lz_j)] + i\sin[2\pi(hx_j + ky_j + lz_j)]\},$$

where $F_{hkl}$ is the structure factor for the reciprocal lattice vector with indices h, k, l; $q_j$ are the occupancy populations of each site; $T_j$ are the temperature factors which correspond to thermal motions; and $f_j$ are the atomic scattering factors. While the populations $q_j$ are constants, the temperature factors $T_j$ and atomic scattering factors $f_j$ decrease as the indices h, k, l increase.

Working from the magnitudes and phases of the structure factors, the electron density and/or atomic positions within the unit cell of the crystal can be determined. Structural determinations using x-ray diffraction data are described in *An Introduction to X-Ray Crystallography* by Michael M. Woolfson, Cambridge University Press (1970, 1997), which is hereby incorporated by reference in its entirety.

In principle, all of the x-ray diffraction reflections are capable of being known or measured (i.e., cognizable). However, due to various aspects of the systems used to experimentally measure the reflection intensities, the set of measured intensities may be incomplete, or may contain errors. First, some x-ray diffraction measurement systems do not provide a measurement of the (0, 0, 0) reflection, which can contain useful information regarding the contents of the crystal. Second, the range of reflections accessible by the x-ray measurement system can be constrained to some value, preventing the measurement of reflections corresponding to larger reciprocal lattice vectors. These larger reciprocal lattice vectors can contain high-resolution information (i.e., corresponding to shorter distances in direct space) regarding the crystal structure. Third, various other reflections may be partially or wholly occluded by various portions of the x-ray diffraction measurement system. Fourth, there may be other experimental factors, such as signal-to-noise, which reduce the confidence of a particular measurement by the x-ray measurement system.

SUMMARY OF THE INVENTION

According to one aspect of the present invention, a method uses linear prediction analysis to define a first structure factor component for a first reflection from x-ray crystallography data. The x-ray crystallography data comprises a set of cognizable reflections. The method comprises expressing the first structure factor component as a first linear equation in which the first structure factor component is equal to a sum of a first plurality of terms. Each term comprises a product of (1) a structure factor component for a cognizable reflection from the x-ray crystallography data, wherein the cognizable reflection has a separation in reciprocal space from the first reflection, and (2) a linear prediction coefficient corresponding to the separation between the cognizable reflection and the first reflection. The method further comprises calculating values for the linear prediction coefficients. The method further comprises substituting the values for the linear prediction coefficients into the first linear equation, thereby defining the first structure factor component for the first reflection.

According to another aspect of the present invention, a method refines x-ray diffraction data. The method comprises deriving a value of a first structure factor from a linear combination of other structure factors.

According to another aspect of the present invention, a computer readable medium has instructions stored thereon which cause a general purpose computer to perform a method of using linear prediction analysis to define a first structure factor component for a first reflection from x-ray crystallography data. The x-ray crystallography data comprises a set of cognizable reflections. The method comprises expressing the first structure factor component as a first linear equation in which the first structure factor component is equal to a sum of a first plurality of terms. Each term comprises a product of (1) a structure factor component for a cognizable reflection from the x-ray crystallography data, wherein the cognizable reflection has a separation in reciprocal space from the first reflection, and (2) a linear prediction coefficient corresponding to the separation between the cognizable reflection and the first reflection. The method further comprises calculating values for the linear prediction coefficients. The method further comprises substituting the values for the linear prediction coefficients into the first linear equation, thereby defining the first structure factor component for the first reflection.

According to another aspect of the present invention, a computer-implemented x-ray crystallography analysis system comprises a structure factor component generator for generating a first structure factor component for a first reflection from x-ray crystallography data using linear prediction analysis. The x-ray crystallography data comprises a set of cognizable reflections. The first structure factor component is expressed as a first linear equation in which the first structure factor component is equal to a sum of a first plurality of terms. Each term comprises a product of (1) a structure factor component for a cognizable reflection from the x-ray crystallography data, wherein the cognizable reflection has a separation in reciprocal space from the first reflection, and (2) a linear prediction coefficient corresponding to the separation between the cognizable reflection and the first reflection. The system further comprises a calculating module for calculating values for the linear prediction coefficients. The system further comprises a resultant structure factor component definer for defining the first structure factor component for the first reflection by substituting the values for the linear prediction coefficients into the first linear equation.

According to another aspect of the present invention, a computer-implemented x-ray crystallography analysis system comprises a means for generating a first structure factor component for a first reflection from x-ray crystallography data using linear prediction analysis. The x-ray crystallography data comprises a set of cognizable reflections. The first structure factor component is expressed as a first linear equation in which the first structure factor component is equal to a sum of a first plurality of terms. Each term comprises a product of (1) a structure factor component for a cognizable reflection from the x-ray crystallography data, wherein the cognizable reflection has a separation in reciprocal space from the first reflection, and (2) a linear prediction coefficient corresponding to the separation between the cognizable reflection and the first reflection. The system further comprises a means for calculating values for the linear prediction coefficients. The system further comprises a means for defining the first structure factor component for the first reflection by substituting the values for the linear prediction coefficients into the first linear equation.

DETAILED DESCRIPTION OF THE PREFERRED EMBODIMENT

Figure 1:
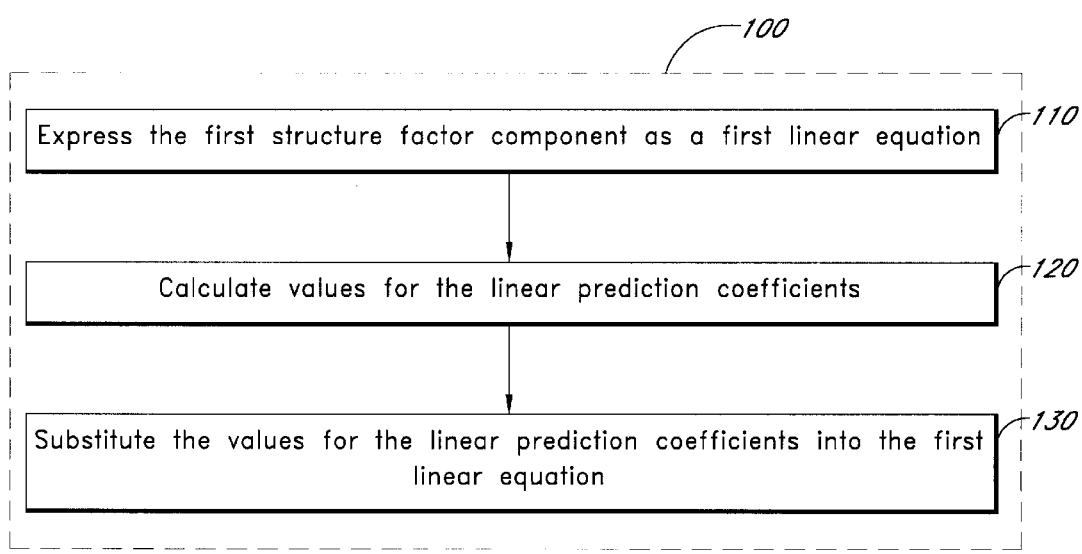
FIG. 1 is a flowchart of one embodiment of a method of using linear prediction analysis to define a first structure factor component for a first reflection from x-ray crystallography data.

In describing embodiments of the invention, the terminology used is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

In many embodiments, the present invention is useful in computer-implemented x-ray crystallography analysis processes. In these processes, x-ray crystallography data are analyzed using software code running on general purpose computers, which can take a wide variety of forms, including, but not limited to, network servers, workstations, personal computers, mainframe computers, and the like. The code which configures the computer to perform these analyses is typically provided to the user on a computer readable medium, such as a CD-ROM. The code may also be downloaded by a user from a network server which is part of a local or wide-area network, such as the Internet.

The general purpose computer running the software will typically include one or more input devices such as a mouse and/or keyboard, a display, and computer readable memory media such as random access memory integrated circuits and a hard disk drive. It will be appreciated that one or more portions, or all of the code may be remote from the user and, for example, resident on a network resource such as a LAN server, Internet server, network storage device, etc. In typical embodiments, the software receives as an input a variety of information, such as the x-ray crystallographic data and any user-determined parameters for the analysis.

As described above, an analysis of x-ray diffraction reflections from a crystal results in an indexed set of complex numbers, called structure factors, from which characteristics of the atomic configuration within the crystal can be derived. In three dimensions, the structure factors $F_{hkl}$ are indexed by a triplet of integer indices h, k, l, which correspond to the three orthogonal directions in reciprocal space. Higher indices correspond to structure factors which provide information with better spatial resolution of the atomic configuration within the crystal.

The nature of the experimental process limits the maximum values of the h, k, and l indices for which structure factors can be accurately derived. In embodiments of the invention, resolution is improved despite experimental limitations by using experimentally determined structure factors to derive approximate values for the structure factors that cannot be or were not experimentally determined. In advantageous embodiments of the invention, the value of an unknown structure factor is derived from a linear combination of other structure factors having experimentally determined values. As described in further detail below, the coefficients of the linear formula used to derive unknown structure factor values are themselves derived from the experimentally determined structure factor values.

FIG. 1 is a flowchart of one embodiment of a method 100 of using linear prediction analysis to define a first structure factor component for a first reflection from x-ray crystallography data. The x-ray crystallography data comprises a set of cognizable reflections. The method 100 comprises expressing the first structure factor component in an operational block 110 as a first linear equation in which the first structure factor component is equal to a sum of a first plurality of terms. Each term comprises a product of (1) a structure factor component for a cognizable reflection from the x-ray crystallography data, wherein the cognizable reflection has a separation in reciprocal space from the first reflection, and (2) a linear prediction coefficient corresponding to the separation between the cognizable reflection and the first reflection. The method 100 further comprises calculating values for the linear prediction coefficients in an operational block 120. The method further comprises substituting the values for the linear prediction coefficients into the first linear equation in an operational block 130, thereby defining the first structure factor component for the first reflection.

In the operational block 110, the first structure factor component is expressed by a first linear equation as equal to a sum of a first plurality of terms. In certain embodiments, the first structure factor component is real or imaginary. Alternatively, in still other embodiments, the first structure factor component is the magnitude or the phase of the corresponding structure factor.

In certain embodiments, the first structure factor component $F_{hkl}$ is expressed as the first linear equation in the following form:

$$\text{Equation 2:}\ F_{hkl} = \sum_{s=1}^{N_{coef}} a_s F_{(h-s\Delta_h)(k-s\Delta_k)(l-s\Delta_l)},$$

where $N_{coef}$ is the number of terms in the sum, and $s\Delta_h$, $s\Delta_k$, $s\Delta_l$, represent the separation along the axes a*, b*, and c* in reciprocal space between the first reflection and the cognizable reflection. To produce accurate values for non-experimentally determined structure factors, the value of $N_{coef}$ is generally at least as large as the number of scatterers in the unit cell, which for protein x-ray crystallography is typically several hundred to a several thousand.

In the form of Equation 2 for the first structure factor component $F_{hkl}$ each term comprises the product of two elements. One element is a structure factor component $F_{(h-s\Delta_h)(k-s\Delta_k)(l-s\Delta_l)}$ for a cognizable reflection from the x-ray crystallography data which is separated in reciprocal space from the first reflection corresponding to the $F_{hkl}$ structure factor component. In certain embodiments, the structure factor components of the sum correspond to adjacent reflections in reciprocal space (for example, $\Delta_h=1$, $\Delta_k=0$, $\Delta_l=0$). Reverse linear prediction corresponds to negative values for one or more of $\Delta_h$, $\Delta_k$, or $\Delta_l$.

The other element is a linear prediction coefficient $a_s$ corresponding to the separation between the cognizable reflection and the first reflection. As is described below, these linear prediction coefficients $a_s$ are initially unknown, but can be solved for using various methods. In the form of Equation 2, the first structure factor component is expressed as a linear equation comprising a linear combination of other structure factor components with indices which are less than the indices for the first structure factor.

As an example of a first linear equation in accordance with embodiments of the present invention, the $F_{Nkl}$ reflection (where k and l are constants) can be expressed as a linear combination of the structure factor components $F_{(N-s)kl}$:

$$\text{Equation 3:}\ F_{Nkl}=a_1 F_{(N-1)kl}+a_2 F_{(N-2)kl}+a_3 F_{(N-3)kl}+\ldots +a_{N_{coef}}F_{(N-{coef})kl}.$$

In this example, the structure factor components $F_{(N-s)kl}$ are selected along a direction parallel to the a* axis in reciprocal space (i.e., $\Delta_h=1$, and $\Delta_k=\Delta_l=0$), and s represents the number of steps along this direction. In certain embodiments, the structure factor components $F_{(N-s)kl}$ are known, but the linear prediction coefficients $a_s$ are not known. While in principle, structure factor components for cognizable reflections with all combinations of $\Delta_h$, $\Delta_k$, $\Delta_l$, can be used in the first linear equation, in certain embodiments, only a subset will be useful due to missing or erroneous experimental data corresponding to certain reflections.

As a simple one-dimensional example, structure factors $F_1$ through $F_{10}$ may be known, and it may be desired to predict the value of $F_{11}$. A series of linear equations may be formed as follows:

As $F_2$ through $F_{10}$ are measured, known values, the three linear prediction coefficients $a_1$, $a_2$, and $a_3$ may be selected so as to force these six equations to be true with a minimum total error. Once these linear prediction coefficients as have been selected, a value for unknown $F_{11}$ is predicted with the formula:

$$\text{Equation 5:}\ F_{11}=a_1 F_{10}+a_2 F_9+a_3 F_8.$$

Several techniques for determining linear prediction coefficients are described in further detail below with reference to FIGS. 2, 3, 4, and 5.

In certain embodiments which use Equation 2 to express the first structure factor component, the separation between the first reflection and each cognizable reflection has the same number of steps along each of the reciprocal space axes a*, b*, and c*, by virtue of using the single index s for all three components of the separation. In other embodiments, two or three indices are used in place of the single index of Equation 2 to include cognizable reflections in the first linear equation which have different numbers of steps along the three reciprocal space axes. Persons skilled in the art are able to express the first structure factor component as a first linear equation in accordance with these embodiments of the present invention.

It will be appreciated by those in the art that a variety of mathematical techniques for selecting a set of linear prediction coefficients as from already measured structure factor values have been developed and may be used in embodiments of the invention. In general, the techniques involve selecting a set of linear prediction coefficients that predicts, with the least total error, a set of the known structure factor values from other known structure factor values using a series of linear equations of the form of Equation 2. This set of linear prediction coefficients is then used in the linear formula of Equation 2 to predict the value of an unknown structure factor component $F_{hkl}$ from other known structure factor values. Such techniques have been applied in communication signal processing and analysis applications, but have never been utilized in the analysis of x-ray diffraction data.

Figure 2:
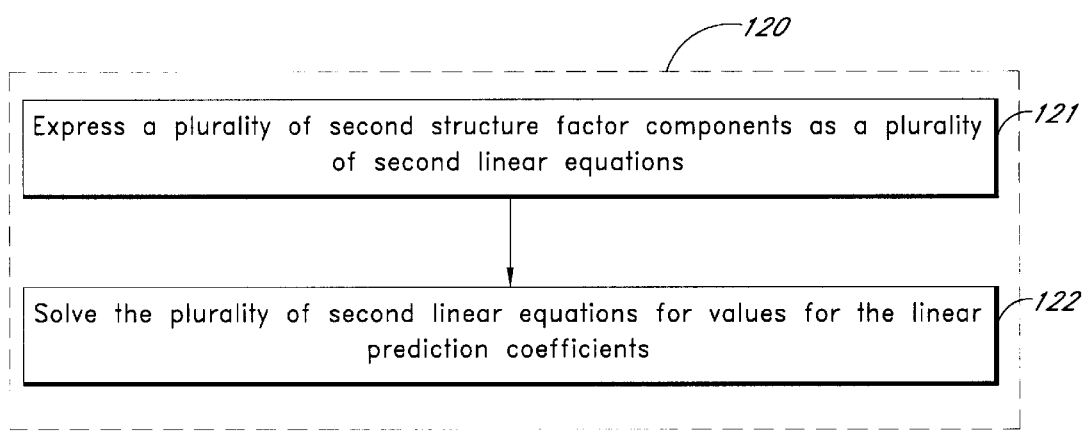
FIG. 2 is a flowchart of one embodiment of calculating values for the linear prediction coefficients.

In the operational block 120, values for the linear prediction coefficients are calculated. FIG. 2 is a flowchart of one embodiment of the calculation corresponding to operational block 120. In the embodiment illustrated in FIG. 2, calculating values for the linear prediction coefficients comprises expressing a plurality of second structure factor components for a plurality of second reflections from the set of cognizable reflections in an operational block 121 as a plurality of second linear equations. In the plurality of second linear equations, each second structure factor component is equal to a sum of a second plurality of terms. Each term comprises a product of (1) a structure factor component for a cognizable reflection from the x-ray crystallography data, wherein the cognizable reflection has a separation in reciprocal space from the second reflection, and (2) the linear prediction coefficient corresponding to the separation between the cognizable reflection and the second reflection. In certain embodiments, each of the second linear equations is similar in form to the first linear equation, using the linear prediction coefficients $a_s$ corresponding to the separation between the cognizable reflection and the second reflection. Calculating values for the linear prediction coefficients further comprises solving the plurality of second linear equations for a set of values for the linear prediction coefficients in an operational block 122.

Continuing the example described above, the plurality of second structure factor components can have the following form:
The second reflections are from the set of cognizable reflections, so each second structure factor component is capable of being measured or known. In embodiments in which the second structure factor components are known, and are expressed as linear combinations of other known structure factor components, the only unknown parameters are the linear prediction coefficients $a_s$.

In the operational block 122, the plurality of second linear equations is solved for a set of values corresponding to the set of coefficients. In embodiments in which there are $N_{coef}$ unknown linear prediction coefficients $a_s$, solving for a set of values utilizes at least $N_{coef}$ independent second linear equations. Persons skilled in the art are able to solve the plurality of second linear equations for the set of values for the linear prediction coefficients $a_s$ in accordance with embodiments of the present invention.

In the operational block 130, the set of values for the linear prediction coefficients $a_s$ are substituted into the first linear equation, thereby defining the first structure factor component $F_{hkl}$ for the first reflection. In this way, the first structure factor component $F_{hkl}$ is then expressed solely in terms of known parameters.

By using the structure factor components for reflections related to the reflection of the structure factor component $F_{hkl}$ to be defined, embodiments of the present invention utilize linear prediction to increase the number of observables used in the optimization of the molecular geometry. A relatively small extension (e.g., 20%) along all lines in reciprocal space will lead to large increases in the number of reflections because the number of reflections within a given volume of reciprocal space defined by a reciprocal lattice vector increases with the cube of the indices h,k,l of the reciprocal lattice vector. For example, an extension of the maximum reciprocal lattice vector from $\sqrt{h^2+k^2+l^2}=20$ to 24 increases the number of reflections available for use in the optimization of the molecular geometry by $(24^3-20^3)/20^3 \approx 70\%$.

Embodiments of the present invention can also extrapolate measured data to higher resolution. Reflections for reciprocal lattice vectors with larger indices h,k,l correspond to longer vectors in reciprocal space, which imply shorter distances in direct space. In this way, a significant improvement in resolution can be achieved. For example, when the length of the unit cell of a hypothetical one-dimensional crystal is a=50 Å, the corresponding reciprocal unit cell edge is a*=0.02 Å$^{-1}$, and the resolution for h=20 is d=2.5 Å. A 20% increase of h (i.e., from 20 to 24) improves the resolution to d=2.08 Å.

Embodiments of the present invention can also be used to complement incomplete or erroneous x-ray crystallography data sets. Embodiments of the present invention can provide a method to detect and replace "outlier" reflections, i.e., measured reflections which, for one reason or another, are aberrant or erroneous. In this way, hidden experimental errors can be identified and eliminated or corrected. Such utility is particularly important with regard to multiple isomorphous replacement (MIR) analysis and multiple anomalous diffraction (MAD) analysis.

With regard to missing reflections, embodiments of the present invention can be used to interpolate to provide the missing reflections and to improve data completion within each resolution shell. This utility of embodiments of the present invention can be important when resolution shells contain too few data for cross-validation. Resolution shells are concentric spheres in reciprocal space, designed so that each shell contains an approximately equal number of reflections. Shells with smaller diameters correspond to lower resolution, while shells with larger diameters correspond to higher resolution. The division of the reciprocal space into resolution shells is equivalent to division of the resolution axis into subintervals. Embodiments of the present invention can also be used to evaluate the zeroth-order reflection $|F_{000}|$ and enable subsequent absolute scaling of the set of measured reflections based on the known total number of electrons in the unit cell.

Figure 3:
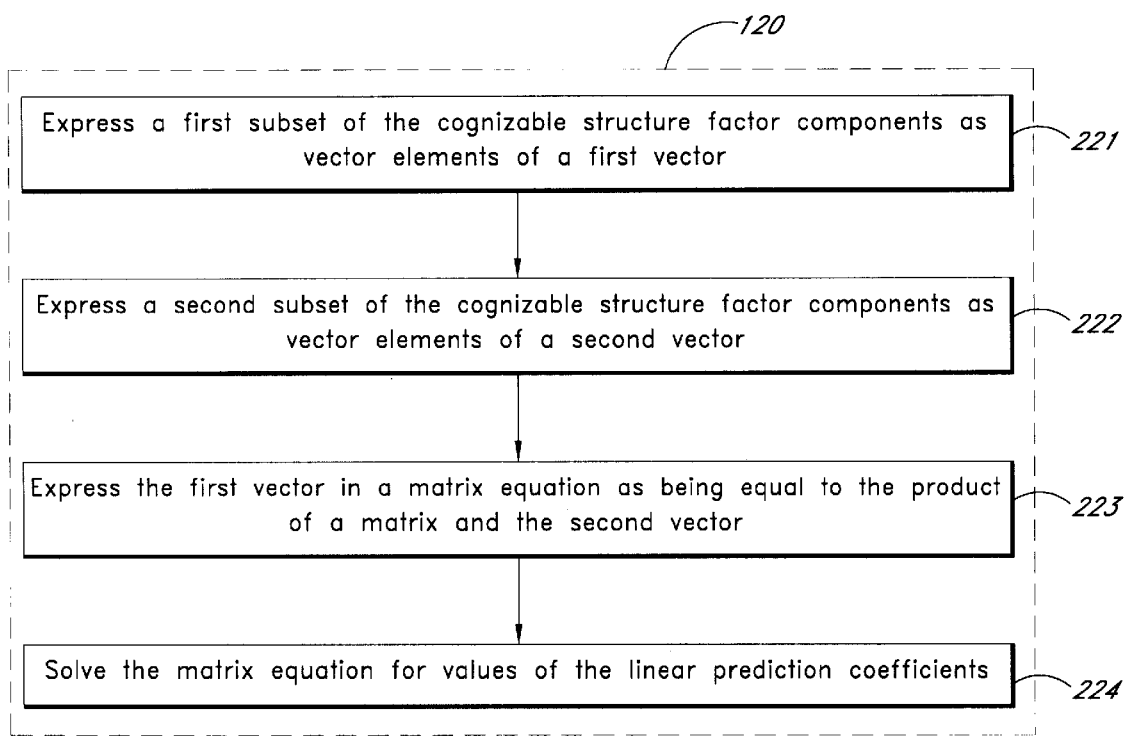
FIG. 3 is a flowchart of another embodiment of calculating values for the linear prediction coefficients.

FIG. 3 is a flowchart of one embodiment of the calculation corresponding to operational block 120. In the embodiment illustrated in FIG. 3, calculating values for the linear prediction coefficients comprises expressing a first subset of the cognizable structure factor components as vector elements of a first vector in an operational block 221. Calculating values for the linear prediction coefficients further comprises expressing a second subset of the cognizable structure factor components as vector elements of a second vector in an operational block 222. Calculating values for the linear prediction coefficients further comprises expressing the first vector in a matrix equation as being equal to the product of a matrix and the second vector in an operational block 223. The matrix comprises the linear prediction coefficients, with each linear prediction coefficient corresponding to a separation in reciprocal space between the cognizable reflection corresponding to one cognizable structure factor component from the first vector and the cognizable reflection corresponding to one cognizable structure factor component from the second vector. Calculating values for the linear prediction coefficients further comprises solving the matrix equation for values of the linear prediction coefficients in an operational block 224.

In certain embodiments, a first subset of the cognizable structure factor components are expressed as vector elements of a first vector in the operational block 221, and a second subset of the cognizable structure factor components are expressed as vector elements of a second vector in the operational block 222. For example, where k and l are constants such as in the example described above, the first vector can have the following form:

Equation 7: $|F_{nkl}> = |F_{(N-1)kl}, F_{(N-2)kl}, F_{(N-3)kl} \ldots >$, and the second vector can have the following form:

Equation 8: $|F_{mkl}> = |F_{(N-2)kl}, F_{(N-3)kl}, F_{(N-4)kl} \ldots >$.

In certain embodiments, the first vector $|F_{nkl}>$ is expressed in the operational block 223 as a matrix equation in which the first vector $|F_{nkl}>$ is equal to the product of a matrix $M_{nm}$ and the second vector $|F_{mkl}>$. Continuing the example from above, the matrix equation can have the following form:

Equation 9:

$$|F_{nkl}\rangle = M_{nm}$$

$$|F_{mkl}\rangle =$$

$$|F_{(N-1)kl}, F_{(N-2)kl}, F_{(N-3)kl}, \ldots\rangle = \begin{Vmatrix} a_1 & a_2 & a_3 & \ldots & \ldots & \ldots \\ 0 & a_1 & a_2 & a_3 & \ldots & \ldots \\ 0 & 0 & a_1 & a_2 & a_3 & \ldots \\ 0 & 0 & 0 & a_1 & a_2 & \vdots \\ \vdots & \vdots & \vdots & \vdots & \vdots & \vdots \end{Vmatrix} |F_{(N-2)kl}, F_{(N-3)kl}, F_{(N-4)kl}, \ldots\rangle$$

In the operational block 224, the matrix equation is solved for values of the linear prediction coefficients. Persons skilled in the art are able to solve the matrix equation and substitute the resulting values into the linear equation in accordance with embodiments of the present invention to define the first structure factor component $F_{hkl}$. Persons skilled in the art are also able to recognize the equivalence of the two embodiments of the example described above.

Figure 4:
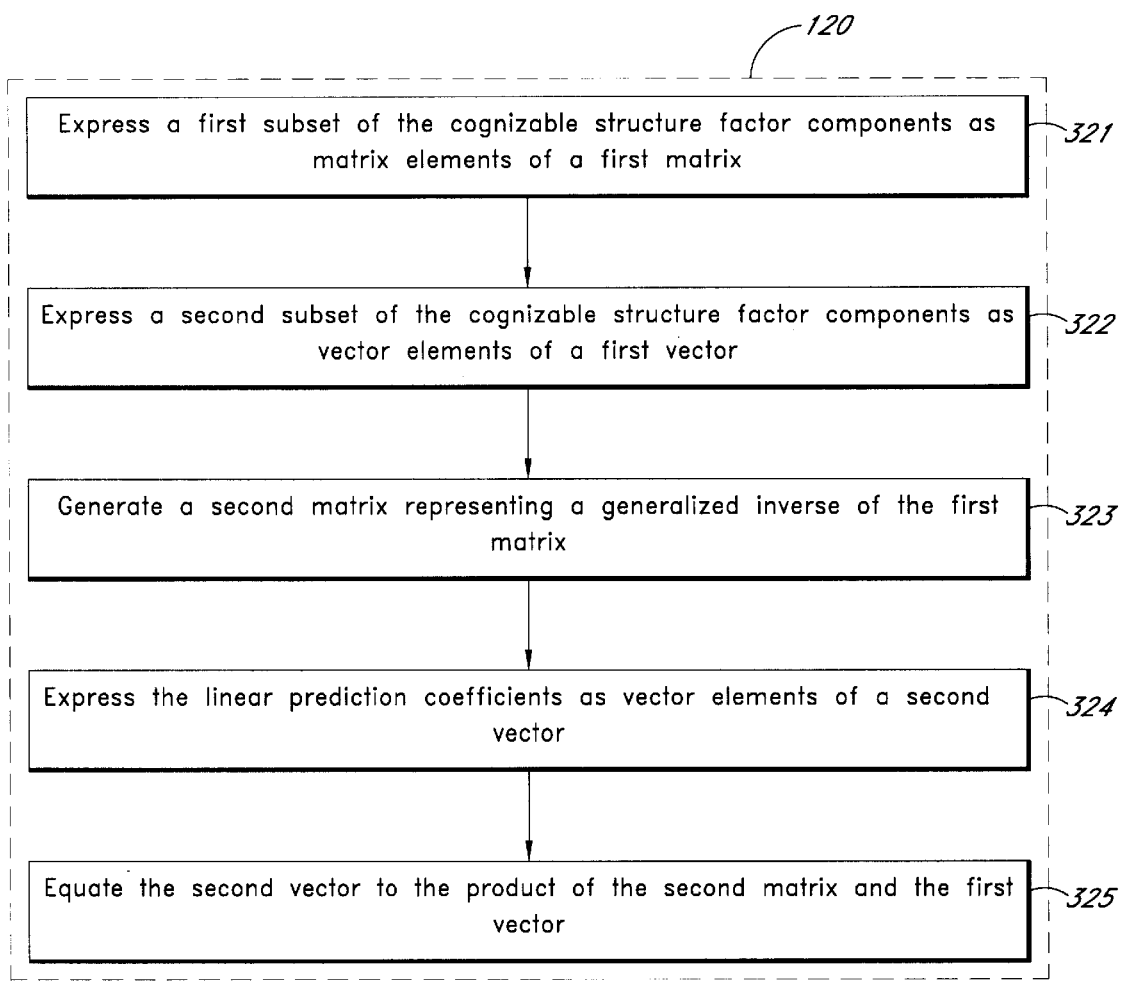
FIG. 4 is a flowchart of another embodiment of calculating values for the linear prediction coefficients.

FIG. 4 is a flowchart of one embodiment of the calculation corresponding to operational block 120. In the embodiment illustrated in FIG. 4, calculating values for the linear prediction coefficients comprises expressing a first subset of the cognizable structure factor components as matrix elements of a first matrix in an operational block 321. Calculating values for the linear prediction coefficients further comprises expressing a second subset of the cognizable structure factor components as vector elements of a first vector in an operational block 322. Calculating values for the linear prediction coefficients further comprises generating a second matrix representing a generalized inverse of the first matrix in an operational block 323. Calculating values for the linear prediction coefficients further comprises expressing the linear prediction coefficients as vector elements of a second vector in an operational block 324. Calculating values for the linear prediction coefficients further comprises equating the second vector to the product of the second matrix and the first vector in an operational block 325, thereby generating values for the linear prediction coefficients.

In certain embodiments, in the operational block 321, a first subset of the cognizable structure factor components is expressed as matrix elements of a first matrix $M_{nm}$, in the operational block 322, a second subset of the cognizable structure factor components is expressed as vector elements of a first vector $|F_{nkl}>$, and in the operational block 324, the linear prediction coefficients $a_s$ are expressed as vector elements of a second vector $|a_s>$. For example, where k and l are constants such as in the example described above, the first matrix $M_{nm}$ can have the following form:

Equation 10: $M_{nm} = ||F_{(n+N_{coef}-m)kl}|n=1, \ldots, (N_{max}-N_{coef}), m=1, \ldots, N_{coef}||$, the first vector can have the following form:

Equation 11: $|F_{nkl}> = |F_{(N_{coef}+1)kl}, F_{N_{max}kl}>$, and the second vector can have the following form:

Equation 12: $|a_s> = |a_1, a_2, \ldots a_{N_{coef}}>$, where $N_{max}$ is typically on the order of tens of thousands.

In certain embodiments, in the operational block 323, the second matrix $(M_{nm})^{-1}$ represents a generalized inverse of the first matrix $M_{nm}$. The values of the linear prediction coefficients $a_s$ are then generated in the operational block 325 by equating the second vector $|a_s>$ to the product of the second matrix $(M_{nm})^{-1}$ and the first vector $|F_{nkl}>$:

Equation 13: $|a_s> = (M_{nm})^{-1} |F_{nkl}>$.

By substituting the values of the coefficients into the linear equation, the first structure factor component for the first reflection can be defined.

Figure 5:
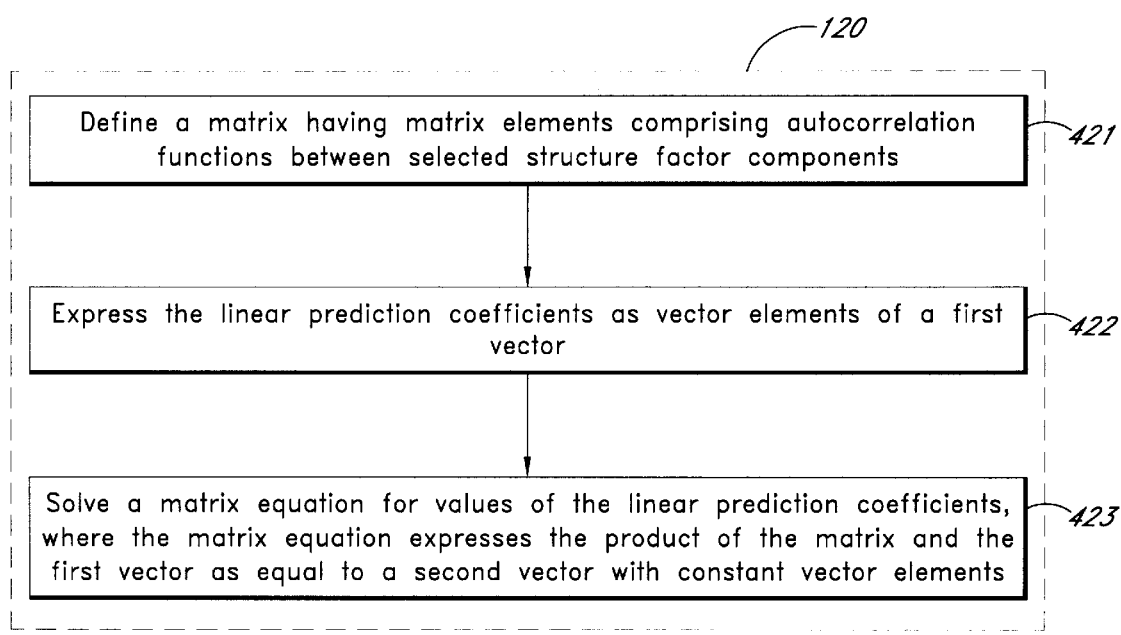
FIG. 5 is a flowchart of another embodiment of calculating values for the linear prediction coefficients.

FIG. 5 is a flowchart of one embodiment of the calculation corresponding to operational block 120. In the embodiment illustrated in FIG. 5, calculating values for the linear prediction coefficients comprises defining a matrix having matrix elements in an operational block 421. Each matrix element comprises an autocorrelation function between selected structure factor components. Calculating values for the linear prediction coefficients further comprises expressing the linear prediction coefficients as vector elements of a first vector in an operational block 422. Calculating values for the linear prediction coefficients further comprises solving a matrix equation for values for the linear prediction coefficients in an operational block 423. The matrix equation expresses the product of the matrix and the first vector as equal to a second vector with constant vector elements.

In certain embodiments, the autocorrelation functions of the matrix in the operational block 421 have the following form:

Equation 14:

$$\Phi_j = \frac{1}{N_{data} + 1 - j}$$

-continued $$\sum_{s=0}^{N_{data}-j} F_{(h-s\Delta_h)(k-s\Delta_k)(l-s\Delta_l)} F_{[h-(s+j)\Delta_h][k-(s+j)\Delta_k][l-(s+j)\Delta_l]}$$

Autocorrelation functions of this form represent autocorrelations between structure factor components along a selected line in reciprocal space.

In certain embodiments, the matrix in the operational block 421 has the following form:

Equation 15:

$$M_{nm} = \begin{Vmatrix} \Phi_0 & \Phi_1 & \Phi_2 & \cdots & \Phi_{N_{coef}} \\ \Phi_1 & \Phi_0 & \Phi_1 & \cdots & \Phi_{N_{coef}-1} \\ \Phi_2 & \Phi_1 & \Phi_0 & \cdots & \Phi_{N_{coef}-2} \\ \vdots & \vdots & \vdots & \ddots & \vdots \\ \Phi_{N_{coef}} & \Phi_{N_{coef}-1} & \Phi_{N_{coef}-2} & \cdots & \Phi_0 \end{Vmatrix}$$

Such a matrix is a symmetric Toeplitz matrix (i.e., a matrix whose elements are constant along diagonals).

In certain embodiments, the linear prediction coefficients $a_s$ are expressed in the operational block 422 as vector elements of the first vector $|1, a_1, a_2, \ldots, a_{N_{coef}}\rangle$, and in the operational block 423, a matrix equation of the following form is solved for values of the linear prediction coefficients:

Equation 16:

$$\begin{Vmatrix} \Phi_0 & \Phi_1 & \Phi_2 & \cdots & \Phi_{N_{coef}} \\ \Phi_1 & \Phi_0 & \Phi_1 & \cdots & \Phi_{N_{coef}-1} \\ \Phi_2 & \Phi_1 & \Phi_0 & \cdots & \Phi_{N_{coef}-2} \\ \vdots & \vdots & \vdots & \ddots & \vdots \\ \Phi_{N_{coef}} & \Phi_{N_{coef}-1} & \Phi_{N_{coef}-2} & \cdots & \Phi_0 \end{Vmatrix} \begin{Vmatrix} 1 \\ a_1 \\ a_2 \\ \vdots \\ a_{N_{coef}} \end{Vmatrix} = \begin{pmatrix} a_0 \\ 0 \\ 0 \\ \vdots \\ 0 \end{pmatrix}.$$

In Equation 16, $a_0$ is a dummy value, as described in "Numerical Recipes in C, The Art of Scientific Programming," by W. H. Press, B. P. Flannery, S. A. Teukolsky, and W. T. Vetterling, Cambridge University Press, Cambridge, 1989, pages 452–464, which is incorporated in its entirety by reference herein.

As with all recursive (i.e., infinite-impulse response) digital filters, solving the matrix equation described above is vulnerable to instabilities and divergences. In certain embodiments, solving the matrix equation of Equation 16 comprises limiting instabilities and divergences by calculating complex roots of a characteristic polynomial equation in a complex plane and forcing all complex roots into a unit circle in the complex plane. Stability is increased by calculating the complex roots of the following characteristic polynomial equation:

Equation 17:

$$z^{N_{coef}} - \sum_{j=1}^{N_{coef}} a_j z^{N_{coef}-j} = 0$$

and forcing all the solutions into the unit circle in the complex plane Z. This result is achieved by moving the roots of the characteristic polynomial onto the unit circle, or more preferably by reflecting them into the unit circle (i.e., by replacing z with $1/z^*$). The linear prediction analysis of embodiments of the present invention extrapolates from the known structure factor components using the characterization of the known structure factor components in terms of the poles in the complex plane, which differs from techniques such as the maximum entropy method.

Figure 6A:
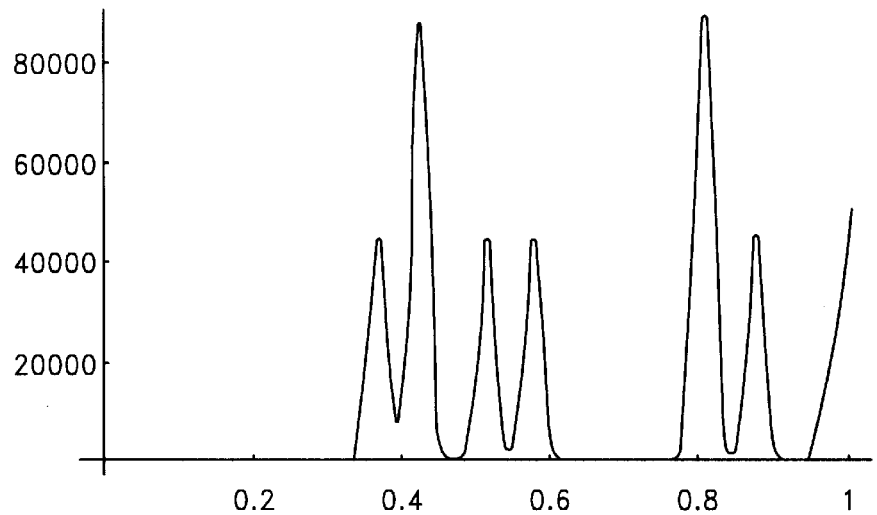
FIG. 6A schematically illustrates an electron distribution of a hypothetical one-dimensional system often atoms.
Figure 6B:
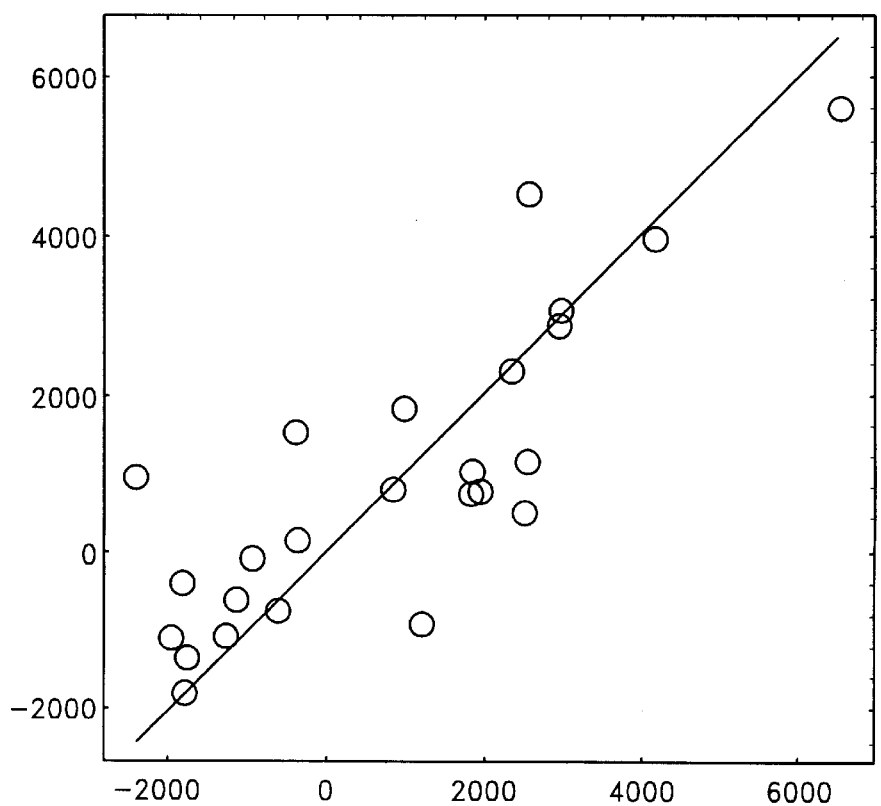
FIG. 6B schematically illustrates the agreement between the true values for the structure factor components corresponding to the electron distribution of FIG. 6A and the corresponding linear prediction estimates from an embodiment of the present invention.
Figure 7A:
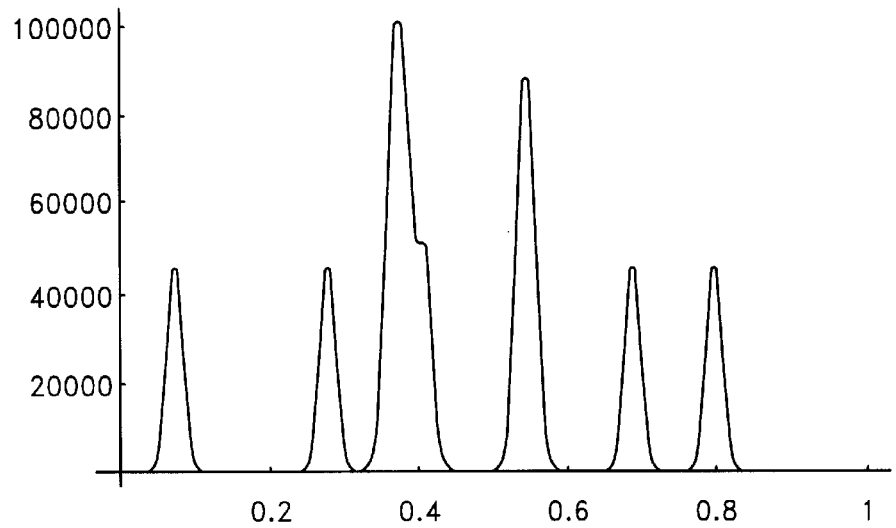
FIG. 7A schematically illustrates another electron distribution of a hypothetical one-dimensional system of ten atoms.
Figure 7B:
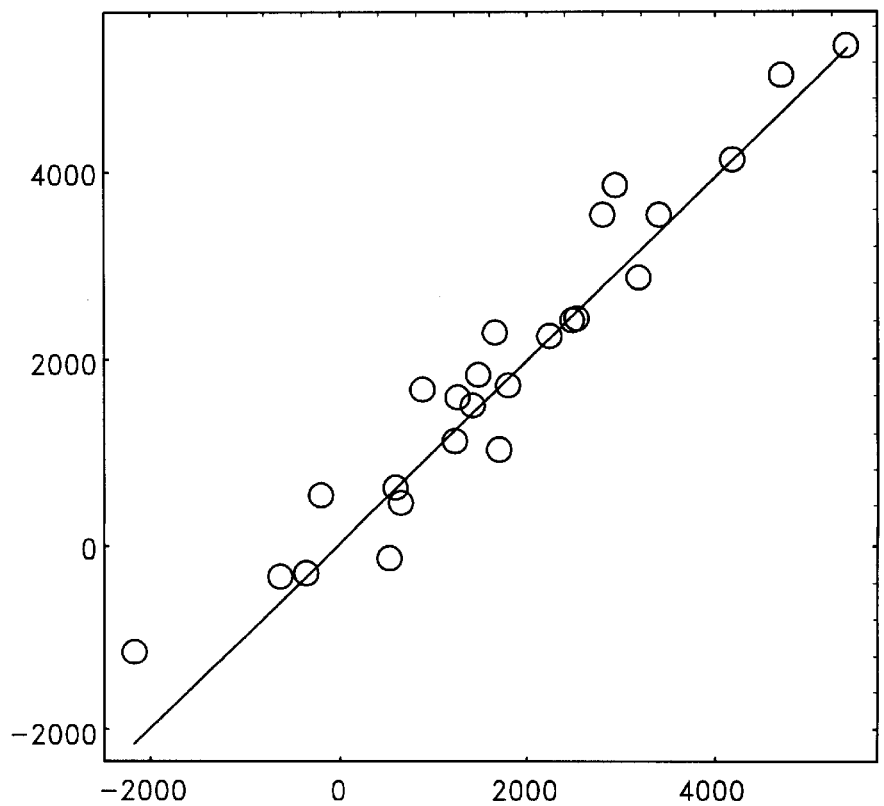
FIG. 7B schematically illustrates the agreement between the true values for the structure factor components corresponding to the electron distribution of FIG. 7A and the corresponding linear prediction estimates from an embodiment of the present invention.

An example of this embodiment is provided by FIGS. 6A and 6B. FIG. 6A schematically illustrates an electron distribution of a hypothetical one-dimensional system of ten atoms along a line segment of unit length. For simplicity, all atoms are assigned unit scattering factors and the temperature factors $T_j$ have been set to facilitate visual inspection. The electron distribution schematically illustrated in FIG. 6A is then used in an embodiment of the present invention to compute a set of 66 structure factor components corresponding to Miller indices h=1, . . . ,66. Structure factor components h=42, . . . ,66 were estimated by means of linear prediction, using the 40 data points h=1, . . . ,40 and 20 poles. FIG. 6B schematically illustrates the agreement between the true values for the structure factor components and the corresponding linear prediction estimates from this embodiment. The resulting agreement has a correlation coefficient of approximately 0.83. Similarly, in another example embodiment of the present invention, FIGS. 7A and 7B schematically illustrate another hypothetical one-dimensional electron distribution and the agreement between the true structure factor components h=42, . . . ,66 and the same structure factor components estimated using linear prediction from structure factor components h=1, . . . ,40 and 20 poles. The resulting agreement has a correlation coefficient of approximately 0.97.

Figure 8A:
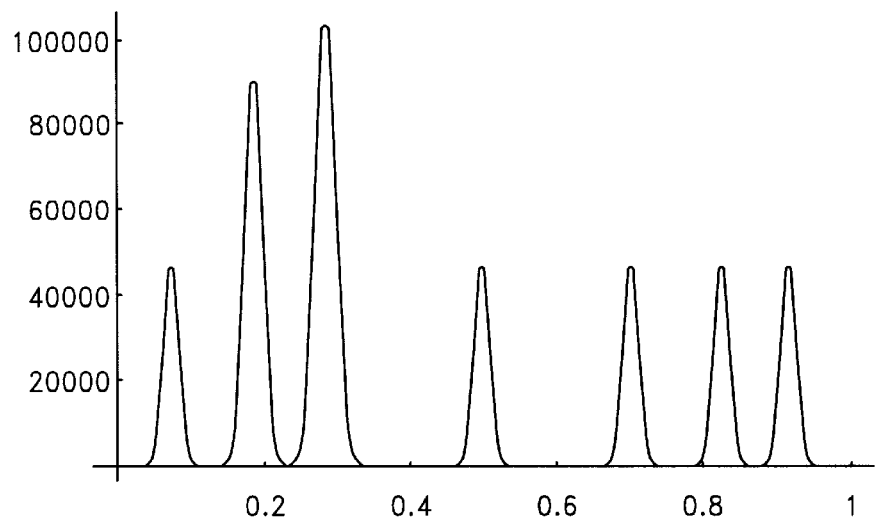
FIG. 8A schematically illustrates another electron distribution of a hypothetical one-dimensional system of ten atoms.
Figure 8B:
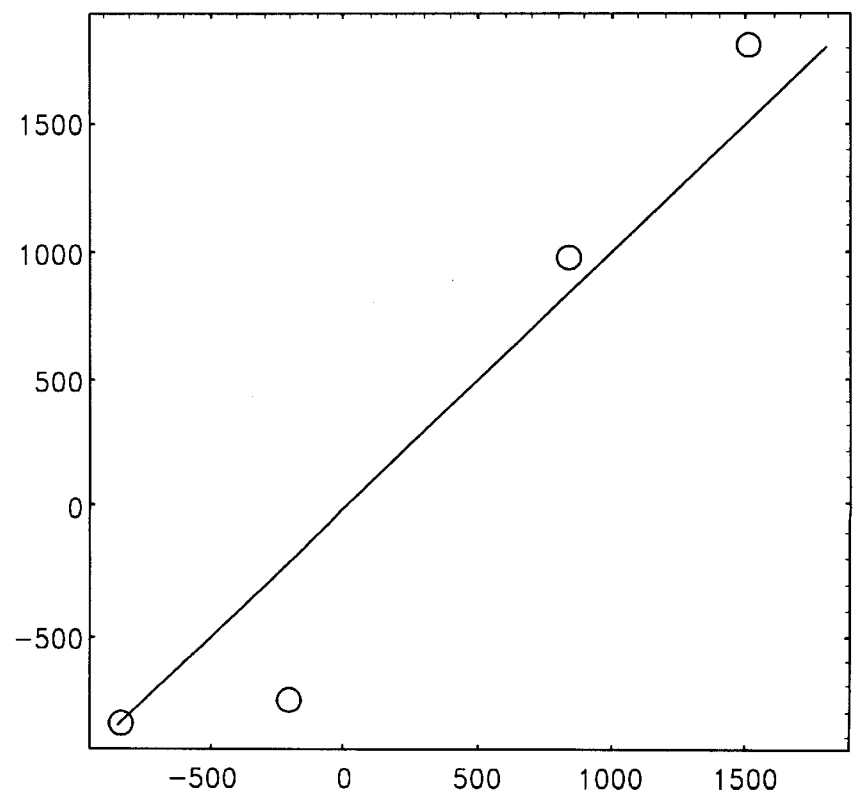
FIG. 8B schematically illustrates the agreement between the true values for the structure factor components corresponding to the electron distribution of FIG. 8A and the corresponding linear prediction estimates from an embodiment of the present invention.

FIG. 8A schematically illustrates another example embodiment of a hypothetical one-dimensional electron distribution with ten atoms. In this embodiment, structure factor components h=27, . . . ,30 were estimated using 25 data points (h=1, . . . ,25) and 20 poles. The resulting agreement between true and estimated structure factor components schematically illustrated in FIG. 8B has a correlation coefficient of approximately 0.98.

Figure 9A:
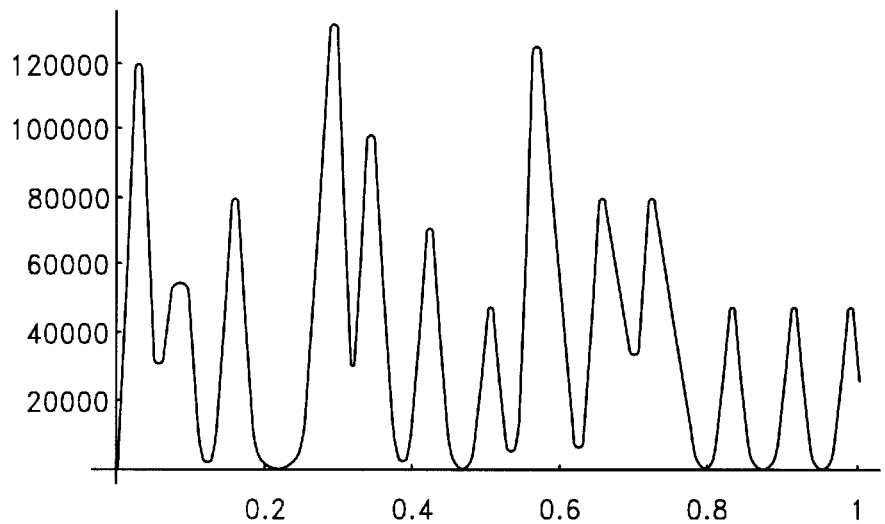
FIG. 9A schematically illustrates another electron distribution of a hypothetical one-dimensional system of thirty atoms.
Figure 9B:
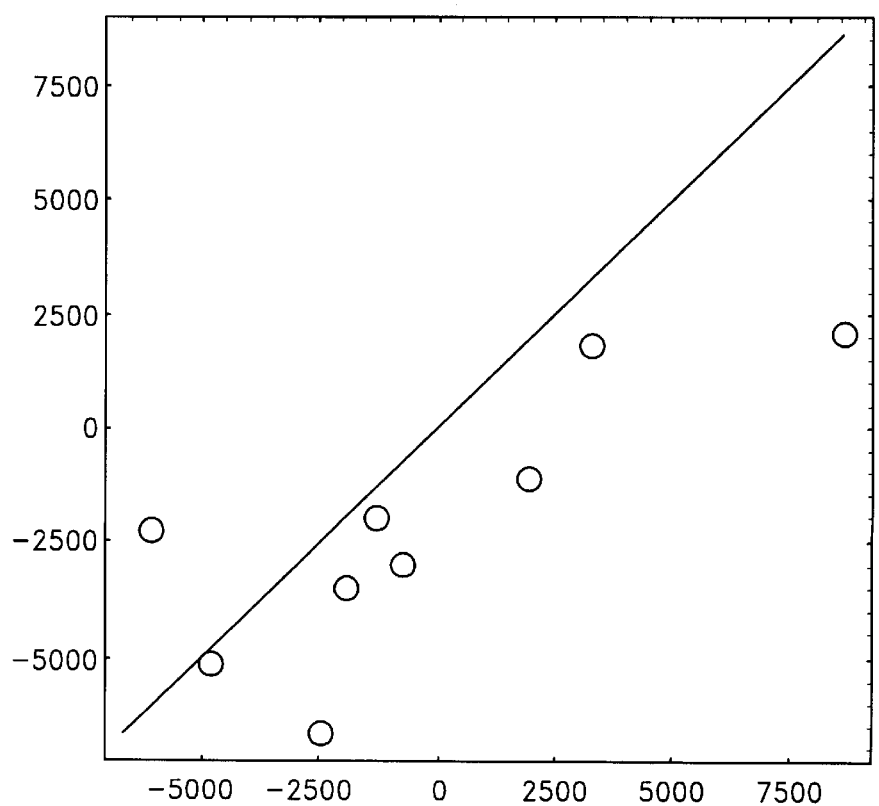
FIG. 9B schematically illustrates the agreement between the true values for the structure factor components corresponding to the electron distribution of FIG. 9A and the corresponding linear prediction estimates from an embodiment of the present invention.

FIG. 9A schematically illustrates another example embodiment of a hypothetical one-dimensional electron distribution with thirty atoms. In this embodiment, structure factor components h=92, . . . ,100 were estimated using 90 data points (h=1, . . . ,90) and 30 poles. The resulting agreement between true and estimated structure factor components schematically illustrated in FIG. 9B has a correlation coefficient of approximately 0.78.

Figure 10A:
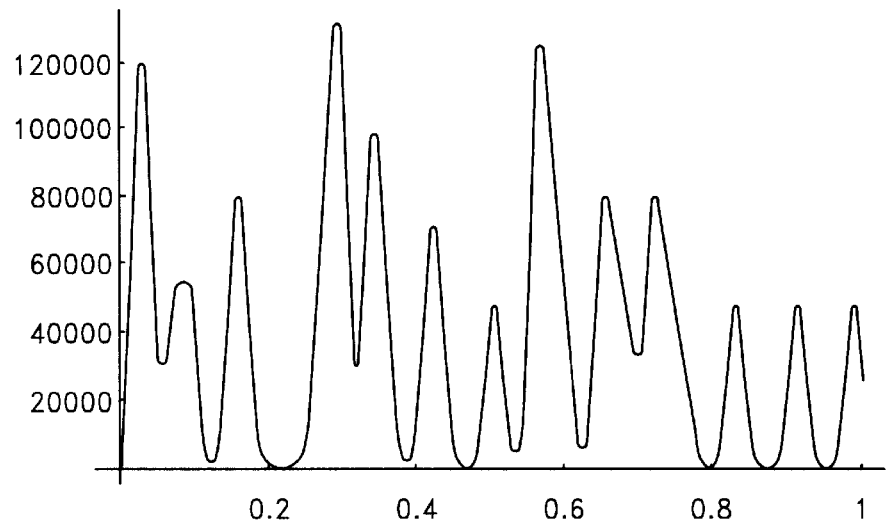
FIG. 10A schematically illustrates another electron distribution of a hypothetical one-dimensional system of thirty atoms.
Figure 10B:
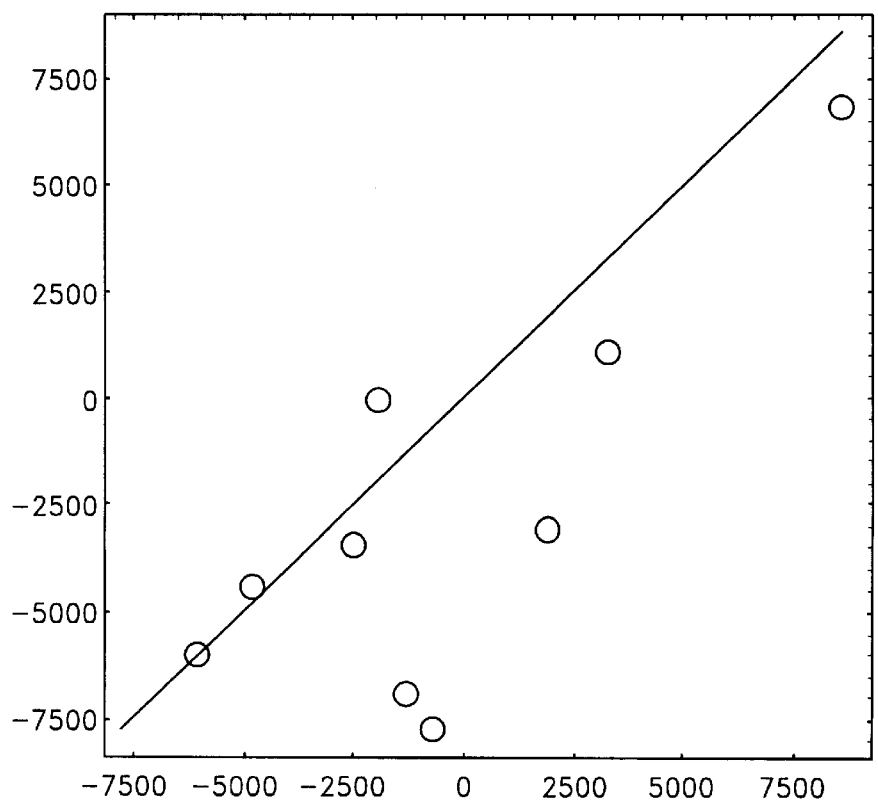
FIG. 10B schematically illustrates the agreement between the true values for the structure factor components corresponding to the electron distribution of FIG. 10A and the corresponding linear prediction estimates from an embodiment of the present invention.

FIG. 10A schematically illustrates another example embodiment of a hypothetical one-dimensional electron distribution with thirty atoms. In this embodiment, structure factor components h=92, . . . ,100 were estimated using 90 data points (h=1, . . . ,90) and 35 poles. The resulting agreement between true and estimated structure factor components schematically illustrated in FIG. 10B has a correlation coefficient of approximately 0.78.

Figure 11A:
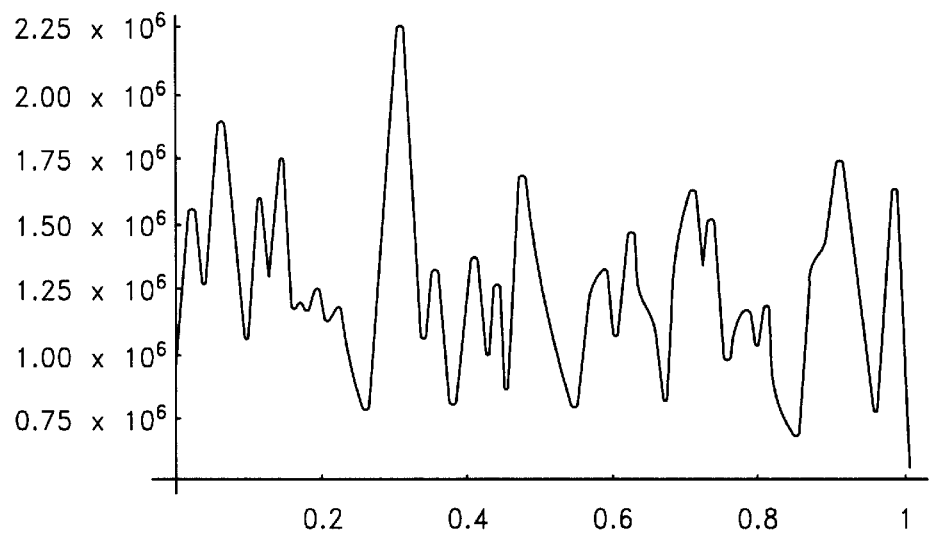
FIG. 11A schematically illustrates another electron distribution of a one-dimensional projection of a hypothetical three-dimensional system of 500 atoms.
Figure 11B:
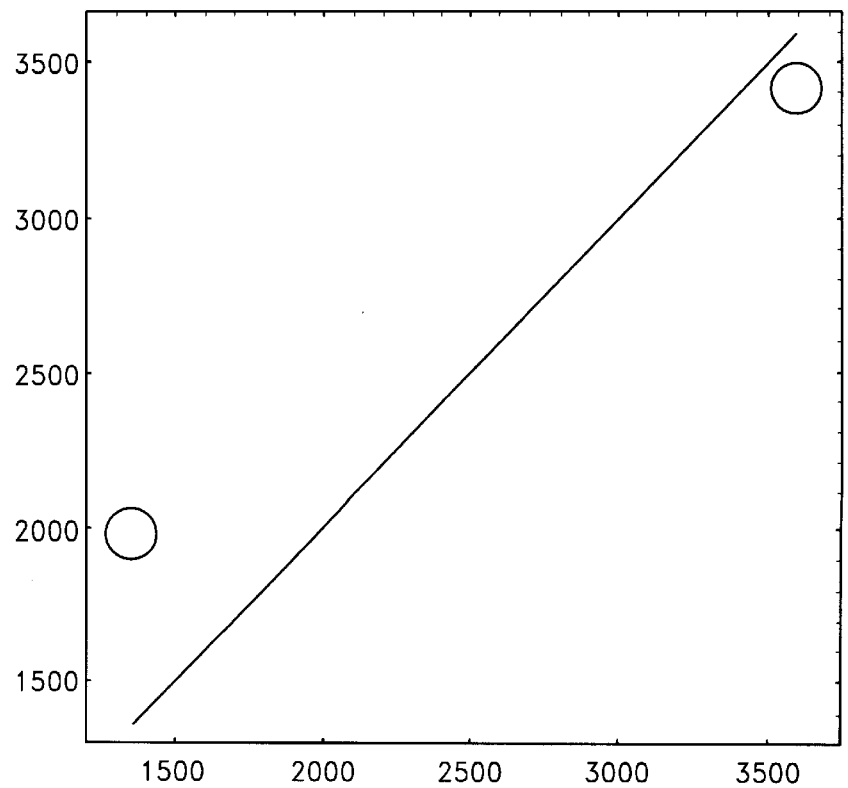
FIG. 11B schematically illustrates the agreement between the true values for the structure factor components corresponding to the electron distribution of FIG. 11A and the corresponding linear prediction estimates from an embodiment of the present invention.

FIG. 11A schematically illustrates an example embodiment of a one-dimensional projection of a hypothetical three-dimensional electron distribution with 500 atoms created in a cube with unit edges. For simplicity, all atoms are assigned unit scattering factors and the temperature factors $T_j$ have been set to facilitate visual inspection. In this embodiment, structure factor components (h, k, l )=(17, 1, 2) and (18, 1, 2) were estimated using 15 data points (h=1, . . . ,15; k=1; l=2) and 5 poles. The resulting agreement between true and estimated structure factor components schematically illustrated in FIG. 11B.

Figure 12A:
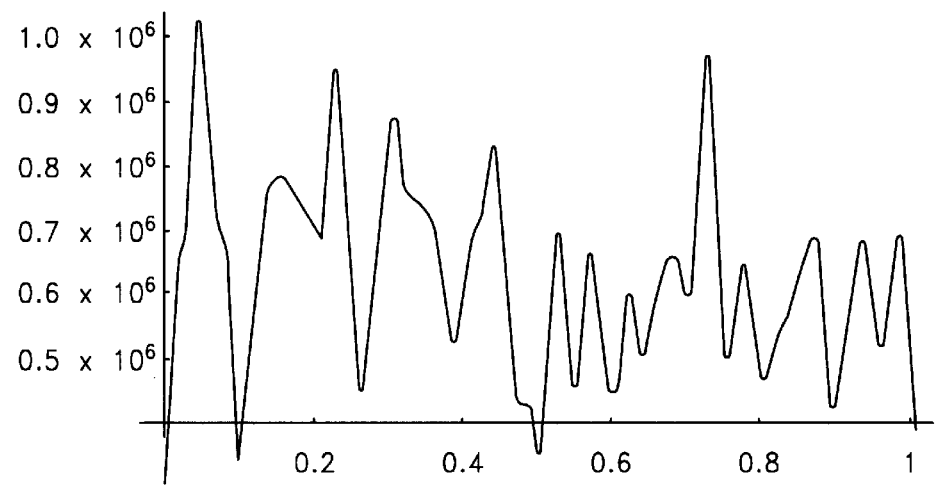
FIG. 12A schematically illustrates another electron distribution of a one-dimensional projection of a hypothetical three-dimensional system of 500 atoms.
Figure 12B:
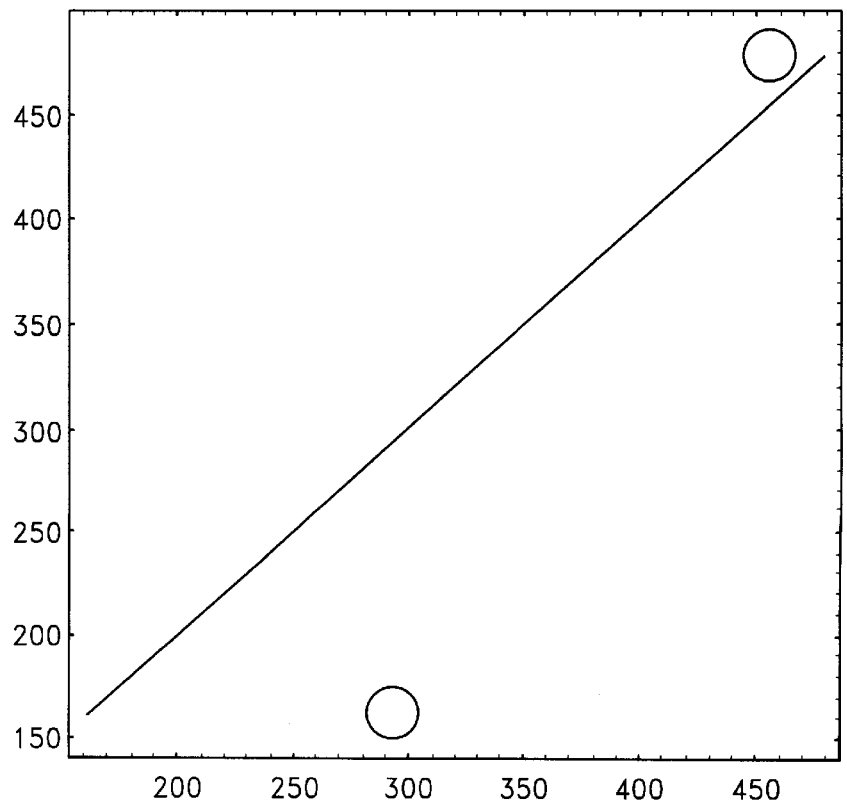
FIG. 12B schematically illustrates the agreement between the true values for the structure factor components corresponding to the electron distribution of FIG. 12A and the corresponding linear prediction estimates from an embodiment of the present invention.

FIG. 12A schematically illustrates another example embodiment of a one-dimensional projection of a hypothetical three-dimensional electron distribution with 500 atoms created in a cube with unit edges. For simplicity, all atoms are assigned unit scattering factors and B-scaling factors equal to 0.01. In this embodiment, structure factor components (h, k, l)=(18, 0, 0) and (19, 0, 0) were estimated using 16 data points (h=1, . . . ,16; k=0; l=0) and 4 poles. The resulting agreement between true and estimated structure factor components is schematically illustrated in FIG. 12B.

Although described above in connection with particular embodiments of the present invention, it should be understood the descriptions of the embodiments are illustrative of the invention and are not intended to be limiting. Various modifications and applications may occur to those skilled in the art without departing from the true spirit and scope of the invention as defined in the appended claims.

What is claimed is:

1. A method of using linear prediction analysis to define a first structure factor component for a first reflection from x-ray crystallography data, the x-ray crystallography data comprising a set of cognizable reflections, the method comprising:

expressing the first structure factor component as a first linear equation in which the first structure factor component is equal to a sum of a first plurality of terms, each term comprising a product of (1) a structure factor component for a cognizable reflection from the x-ray crystallography data, wherein the cognizable reflection has a separation in reciprocal space from the first reflection, and (2) a linear prediction coefficient corresponding to the separation between the cognizable reflection and the first reflection;

calculating values for the linear prediction coefficients; and substituting the values for the linear prediction coefficients into the first linear equation, thereby defining the first structure factor component for the first reflection.

2. The method of claim 1, wherein the first structure factor component is real.

3. The method of claim 1, wherein the first structure factor component is imaginary.

4. The method of claim 1, wherein the first structure factor component is a magnitude.

5. The method of claim 1, wherein the first structure factor component is a phase.

6. The method of claim 1, wherein calculating values for the linear prediction coefficients comprises:

expressing a plurality of second structure factor components for a plurality of second reflections from the set of cognizable reflections as a plurality of second linear equations in which each second structure factor component is equal to a sum of a second plurality of terms, each term comprising a product of (1) a structure factor component for a cognizable reflection from the x-ray crystallography data, wherein the cognizable reflection has a separation in reciprocal space from the second reflection, and (2) the linear prediction coefficient corresponding to the separation between the cognizable reflection and the second reflection; and solving the plurality of second linear equations for the values for the linear prediction coefficients.

7. The method of claim 1, wherein calculating values for the linear prediction coefficients comprises:

expressing a first subset of the cognizable structure factor components as vector elements of a first vector;

expressing a second subset of the cognizable structure factor components as vector elements of a second vector;

expressing the first vector in a matrix equation as being equal to the product of a matrix and the second vector, wherein the matrix comprises matrix elements comprising the linear prediction coefficients, such that each matrix element comprises the linear prediction coefficient corresponding to a separation in reciprocal space between a corresponding cognizable reflection from the second vector and a corresponding cognizable reflection from the first vector; and solving the matrix equation for values of the linear prediction coefficients.

8. The method of claim 1, wherein calculating values for the linear prediction coefficients comprises:

expressing a first subset of the cognizable structure factor components as matrix elements of a first matrix;

expressing a second subset of the cognizable structure factor components as vector elements of a first vector;

generate a second matrix representing a generalized inverse of the first matrix;

expressing the linear prediction coefficients as vector elements of a second vector; and equating the second vector to the product of the second matrix and the first vector, thereby generating the values for the linear prediction coefficients.

9. The method of claim 1, wherein calculating values for the linear prediction coefficients comprises:

defining a matrix having matrix elements, each matrix element comprising an autocorrelation function between selected structure factor components;

expressing the linear prediction coefficients as vector elements of a first vector;

solving a matrix equation for values for the linear prediction coefficients, the matrix equation expressing the product of the matrix and the first vector as equal to a second vector with constant vector elements.

10. The method of claim 9, wherein the matrix elements are constant along diagonals of the matrix.

11. The method of claim 9, wherein solving the matrix equation comprises limiting instabilities and divergences by calculating complex roots of a characteristic polynomial equation in a complex plane and forcing all complex roots into a unit circle in the complex plane.

12. A method of refining x-ray diffraction data comprising deriving a value of a first structure factor from a linear combination of other structure factors.

13. The method of claim 12, wherein said other structure factors comprise a series of structure factors which are adjacent to said first structure factor in reciprocal space.

14. A computer readable medium having instructions stored thereon which cause a general purpose computer to perform a method of using linear prediction analysis to define a first structure factor component for a first reflection from x-ray crystallography data, the x-ray crystallography data comprising a set of cognizable reflections, the method comprising:

expressing the first structure factor component as a first linear equation in which the first structure factor component is equal to a sum of a first plurality of terms, each term comprising a product of (1) a structure factor component for a cognizable reflection from the x-ray crystallography data, wherein the cognizable reflection has a separation in reciprocal space from the first reflection, and (2) a linear prediction coefficient corresponding to the separation between the cognizable reflection and the first reflection;

calculating values for the linear prediction coefficients; and substituting the values for the linear prediction coefficients into the first linear equation, thereby defining the first structure factor component for the first reflection.

15. A computer-implemented x-ray crystallography analysis system comprising:

a structure factor component generator for generating a first structure factor component for a first reflection from x-ray crystallography data using linear prediction analysis, the x-ray crystallography data comprising a set of cognizable reflections, the first structure factor component expressed as a first linear equation in which the first structure factor component is equal to a sum of a first plurality of terms, each term comprising a product of (1) a structure factor component for a cognizable reflection from the x-ray crystallography data, wherein the cognizable reflection has a separation in reciprocal space from the first reflection, and (2) a linear prediction coefficient corresponding to the separation between the cognizable reflection and the first reflection;

a calculating module for calculating values for the linear prediction coefficients; and a resultant structure factor component definer for defining the first structure factor component for the first reflection by substituting the values for the linear prediction coefficients into the first linear equation.

16. A computer-implemented x-ray crystallography analysis system comprising:

a means for generating a first structure factor component for a first reflection from x-ray crystallography data using linear prediction analysis, the x-ray crystallography data comprising a set of cognizable reflections, the first structure factor component expressed as a first linear equation in which the first structure factor component is equal to a sum of a first plurality of terms, each term comprising a product of (1) a structure factor component for a cognizable reflection from the x-ray crystallography data, wherein the cognizable reflection has a separation in reciprocal space from the first reflection, and (2) a linear prediction coefficient corresponding to the separation between the cognizable reflection and the first reflection;

a means for calculating values for the linear prediction coefficients; and a means for defining the first structure factor component for the first reflection by substituting the values for the linear prediction coefficients into the first linear equation.

* * * * *